(12) United States Patent
Chiang et al.

(10) Patent No.: US 6,453,497 B1
(45) Date of Patent: Sep. 24, 2002

(54) ORAL CARE DEVICE

(75) Inventors: Casper Wein-Tien Chiang, Danville; Andy Yang, Concord; Ben Wang, Pacifica, all of CA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/526,678

(22) Filed: Mar. 16, 2000

(51) Int. Cl.[7] .................................................. A46B 7/06
(52) U.S. Cl. ............................. 15/22.1; 15/201; 134/6
(58) Field of Search ..................... 15/22.1, 22.2, 15/22.4, 24, 25, 29, 201, 203, 205.2; 134/6

(56) References Cited

U.S. PATENT DOCUMENTS

| | | |
|---|---|---|
| 2,263,802 A | 11/1941 | Grusin |
| 3,152,349 A | 10/1964 | Brennesholtz |
| 4,709,438 A | 12/1987 | De Tavares |
| 5,309,590 A * | 5/1994 | Giuliani et al. |
| 5,315,732 A | 5/1994 | Huefner et al. |
| 5,321,866 A * | 6/1994 | Klupt |
| 5,327,608 A | 7/1994 | Kosakewich |
| 5,357,644 A | 10/1994 | Theriault |
| 5,398,366 A | 3/1995 | Bradley |
| 5,435,032 A | 7/1995 | McDougall |
| 5,504,958 A * | 4/1996 | Herzog |
| 5,561,881 A | 10/1996 | Klinger et al. |
| 5,778,474 A * | 7/1998 | Shek |
| 5,784,742 A | 7/1998 | Giuliani et al. |
| 5,813,079 A | 9/1998 | Halm |
| 5,839,148 A | 11/1998 | Volpenhein |
| 6,148,462 A * | 11/2000 | Zseng |
| 6,161,245 A | 12/2000 | Weihrauth ................. 125/201 |

FOREIGN PATENT DOCUMENTS

| | | |
|---|---|---|
| DE | 39 28919 A1 | 3/1991 |
| RU | 1752336 A1 | 5/1990 |

* cited by examiner

*Primary Examiner*—Terrence R. Till
(74) *Attorney, Agent, or Firm*—David A. Howley

(57) ABSTRACT

An oral care device includes a handle, a head extending from the handle, and one or more oral care elements extending from the head. The device also includes a drive for engaging a base portion of each of the one or more oral care elements and for positioning each oral care element relative to that portion of the head from which the oral care element projects based on the motion of the oral care device. In a preferred embodiment of the invention, each oral care element is a tuft of one or more bristles.

15 Claims, 5 Drawing Sheets

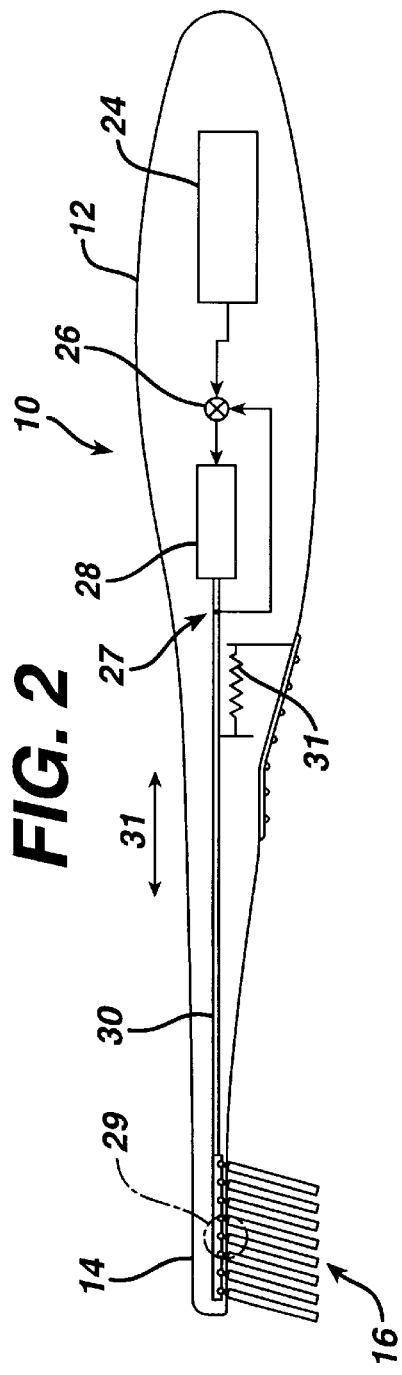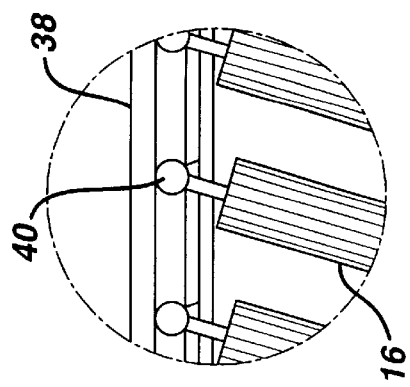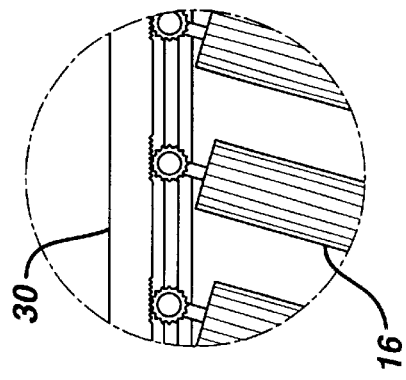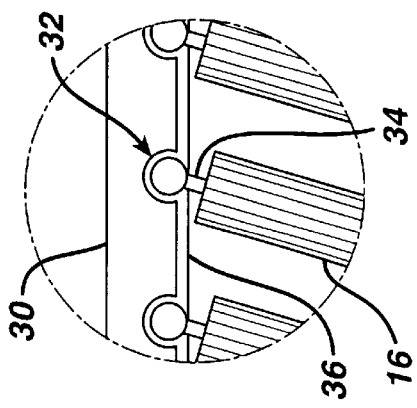
FIG. 2
FIG. 2A
FIG. 2B
FIG. 2C

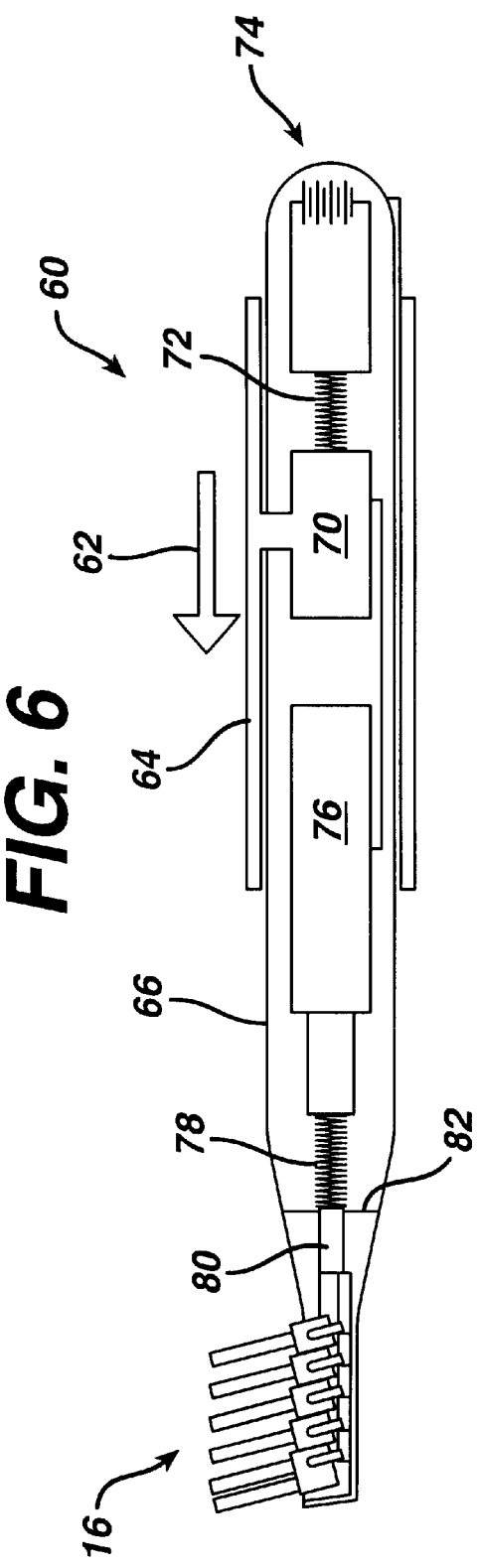
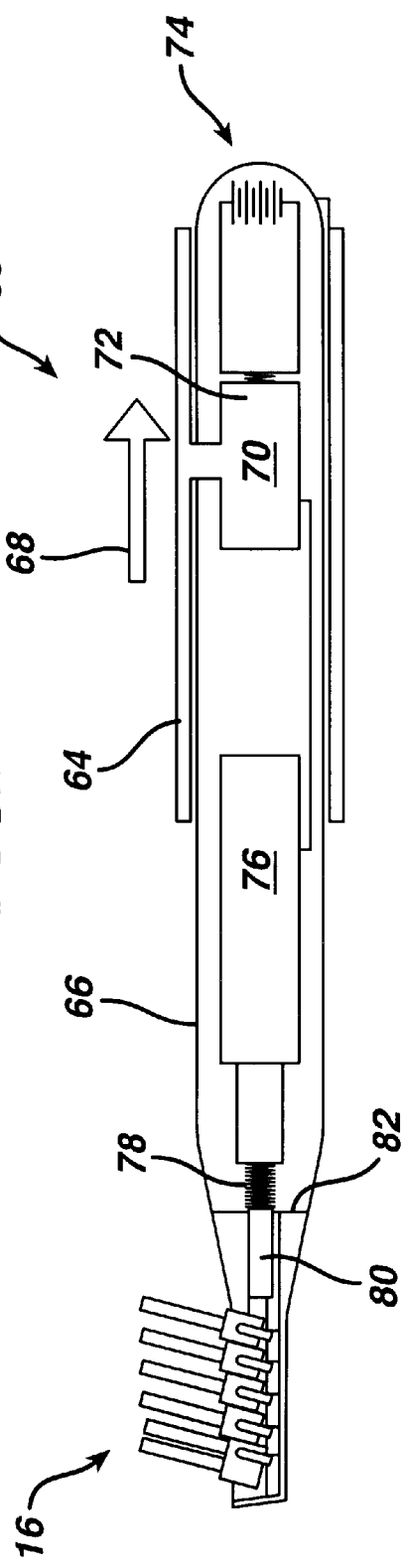

ORAL CARE DEVICE

FIELD OF THE INVENTION

The invention relates generally to the field of oral care, and in particular to an oral care device.

BACKGROUND OF THE INVENTION

Generally speaking, there are two types of brushes used to clean teeth. The first type is an electric toothbrush in which tufts of bristles are automatically oscillated in a rotary or linear manner. The second type is a manual toothbrush wherein movement of the bristles is provided by the user of the brush moving the brush's handle. With both types of brushes each tuft of bristles is typically rigidly fixed to the head of the toothbrush and cannot be adjusted in position relative to the portion of the head to which the tuft is secured.

Oral-B's® CrossAction™ toothbrush has three rows of tufts which are tilted at an acute angle relative to the head either towards (1 row) or away (2 rows) from the handle. The bristles in tufts which are tilted towards the direction of motion of the brush are able to penetrate the interproximal area, bend, and slide across the interproximal area, thereby providing superior plaque removal. However, because the angle of the tuft relative to the head is fixed, the tufts are only tilted towards the direction of motion of the brush for half or less of the brushing strokes. As a result, optimal cleaning of the teeth is not achieved.

U.S. Pat. No. 5,435,032 discloses a toothbrush having a head with a hollow body 16 closed at one side by a flexible membrane 13 formed with cavities 17 to hold bases of tufts of bristles. The cavities form protrusions extending up inside the body 16 which are pushed against by a reciprocating finger 18 to tilt and move the bristles relative to the body 16. The bristle tilting and movement is done constantly and is not based on the motion of the toothbrush itself. As a result, the bristles do not lean in the direction of brush motion during the entire period of brush motion.

SUMMARY OF THE INVENTION

The present invention is directed to overcoming one or more of the problems set forth above. Briefly summarized, according to one aspect of the present invention, an oral care device includes a handle, a head extending from the handle, and one or more oral care elements extending from the head. The device also includes a drive for engaging a base portion of each of the one or more oral care elements and for positioning each oral care element relative to that portion of the head from which the oral care element projects based on the motion of the oral care device. In a preferred embodiment of the invention, each oral care element is a tuft of one or more bristles.

By positioning each oral care element (e.g. tuft of 1 or more bristles) based on the motion of the oral care device, the oral care elements can be optimally positioned to enhance the quality of care provided by the device. For example, all the tufts of bristles on a toothbrush can be leaned into the direction of motion of the brush for each brush stroke to maximize tooth cleaning effectiveness.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 1A is a top view of the head of FIG. 1 with part of the head removed to facilitate viewing;

FIGS. 1B and C show the head portion of FIG. 1 with tufts of bristles shown in alternate positions;

FIG. 2 is a side sectional view of the toothbrush of FIG. 1;

FIGS. 2A–2C are blow-up alternatives for a portion of FIG. 2;

FIGS. 6 and 7 show a further alternative embodiment of the invention.

DETAILED DESCRIPTION OF THE INVENTION

Figure 1:
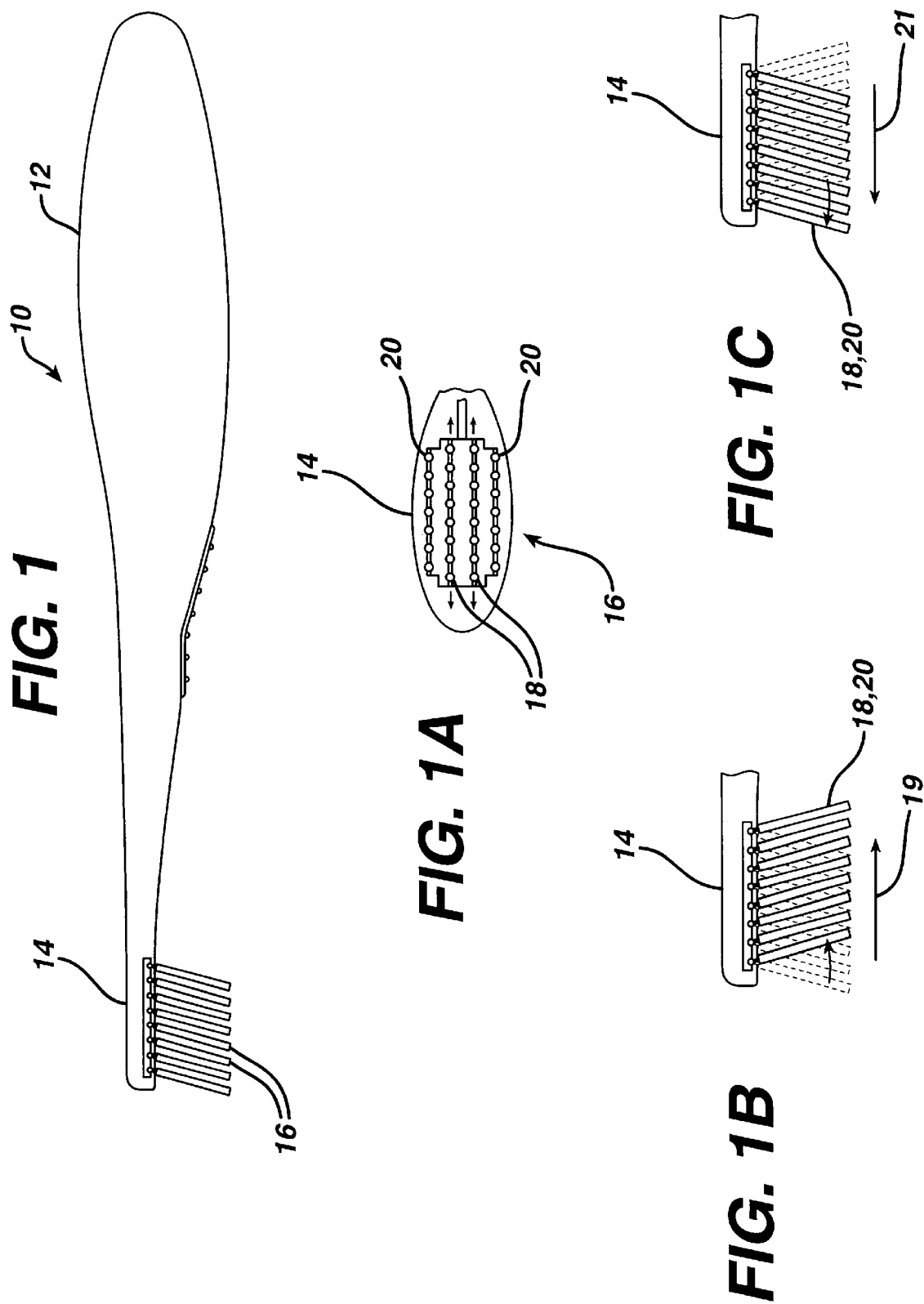
FIG. 1 is a side view of a toothbrush with part of the head removed to facilitate viewing.

Beginning with FIG. 1 and 1A–1C, a toothbrush 10 includes a handle 12 from which extends a head 14. Tufts of one or more bristles 16, extend from head 14. FIG. 1A shows that there are four rows of bristles. Two inner rows of tufts 18 and two outer rows of tufts 20 are movable in two directions indicated by the arrows at the end of each of rows 18 between two positions shown in FIGS. 1B and 1C. FIG. 1B shows the tufts being moved from their position in FIG. 1 (dashed lines) leaning away from handle 12 to a position leaning towards the handle. FIG. 1C shows the tufts being moved from their position in FIG. 1B (dashed lines) leaning towards the handle 12 to a position leaning away from the handle.

When tufts 16 are in either of the positions shown in FIGS. 1B or 1C, they are preferably angled at between about 17 to about 20 degrees from a line (not shown) perpendicular to the surface of head 14 through which the tufts project. Tufts 16 are positioned as in FIG. 1B when a motion sensor (described in further detail below) in handle 12 detects that the toothbrush has started moving in the direction of an arrow 19. As such, tufts 18 are angled into the direction of motion of the toothbrush and provide enhanced cleaning of the teeth. The tufts of bristles are held in that angled position until the direction of motion of the toothbrush is reversed. When the motion sensor detects that the toothbrush has started moving in the direction of an arrow 21 (FIG. 1C), tufts 16 are moved to the position shown in FIGS. 1 and 1C and held in that position to the end of the brush stroke.

Turning to FIGS. 2 and 2A–2C, the mechanism for positioning tufts 16 will be described. In FIG. 2, a bi-directional motion sensor 24 detects when the direction of motion of brush 10 has changed and signals a microprocessor 26. The microprocessor, in response, controls operation of a drive mechanism 28, such as a solenoid, to move a drive shaft 30 in one or the other direction represented by double-headed arrow 31. Movement of the drive shaft moves bristle tufts 16 to either of two positions described above. Electrical power is provided by, for example, a AAA battery (not shown). A feedback sensor 27 informs microprocessor 26 about the position of shaft 30.

In FIG. 2, drive mechanism 28 (e.g. a solenoid) has been deenergized, and a tension spring 31 has pulled shaft 30 to the right to position bristle tufts 16 as shown. Such positioning of the bristle tufts occurs as brush 10 begins to move towards the left in FIG. 2. When the brush stroke changes direction towards the right, motion sensor 24 signals microprocessor 26 which energizes drive mechanism 28. The system is designed such that the drive mechanism overcomes the force of spring 31 and moves shaft 30 to the left, thus rotating bristles 16 to the position shown in FIG. 1B.

Again, at the beginning of a longitudinal brush stroke, tufts 16 are tilted or leaned into the direction of motion and held in that position until the end of the stroke. When the brush starts moving in the opposite direction, the bristles are again moved (rotated) so that they are leaning into the new direction of motion during the entire return stroke.

FIGS. 2A–2C are blow up alternatives to portion 29 of FIG. 2 and disclose various interfaces between drive shaft 30 and bristles 16. FIG. 2A shows a ball and socket interface 32. When drive shaft 32 is moved, it moves the balls of the ball joints, the balls being captured but rotateable in sockets in the drive shaft. A base portion 34 of each tuft is surrounded by a top portion 36 of the head of the toothbrush. As a result, bristles 16 are rotated about base portion 34.

FIG. 2B discloses a rack and pinion arrangement for moving the bristles. Shaft 30 includes teeth which engage a tiny gear secured to the base of each tuft to rotate the tuft in opposite directions. FIG. 2C shows a pivot plate 38, extending from shaft 30, which frictionally engages spheres or cylinders 40 to rotate tufts 16 as the plate is moved back and forth.

Figure 3:
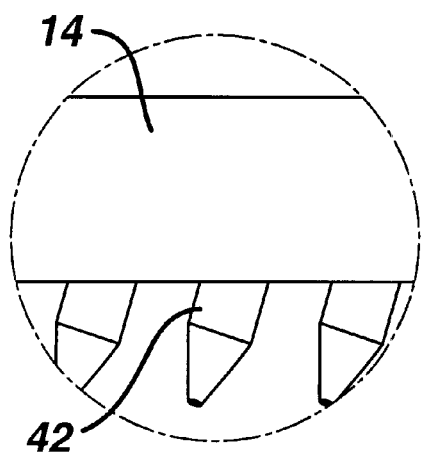
FIGS. 3 and 4 show alternative oral care elements.
Figure 4:
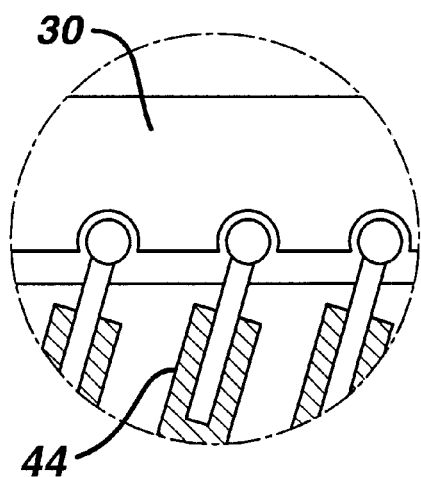

FIGS. 3 and 4 are further blow ups to portion 29 of FIG. 2 and disclose oral care elements which can be used instead of or in conjunction with bristle tufts 16. FIG. 3 discloses a powered nozzle 42 which is used to project an oral care substance into the oral cavity. This substance can be, for example, a jet of water, ultrasonic energy, an anti-bacterial laser or an anti-bacterial gas.

FIG. 4 tufts which are made up of a single bristle 44. This bristle is designed to penetrate into the interdental spaces and is preferably about 0.020 inches in diameter. The bristle can have a plastic (e.g. nylon) core with a gel or foam sheath.

Figure 5:
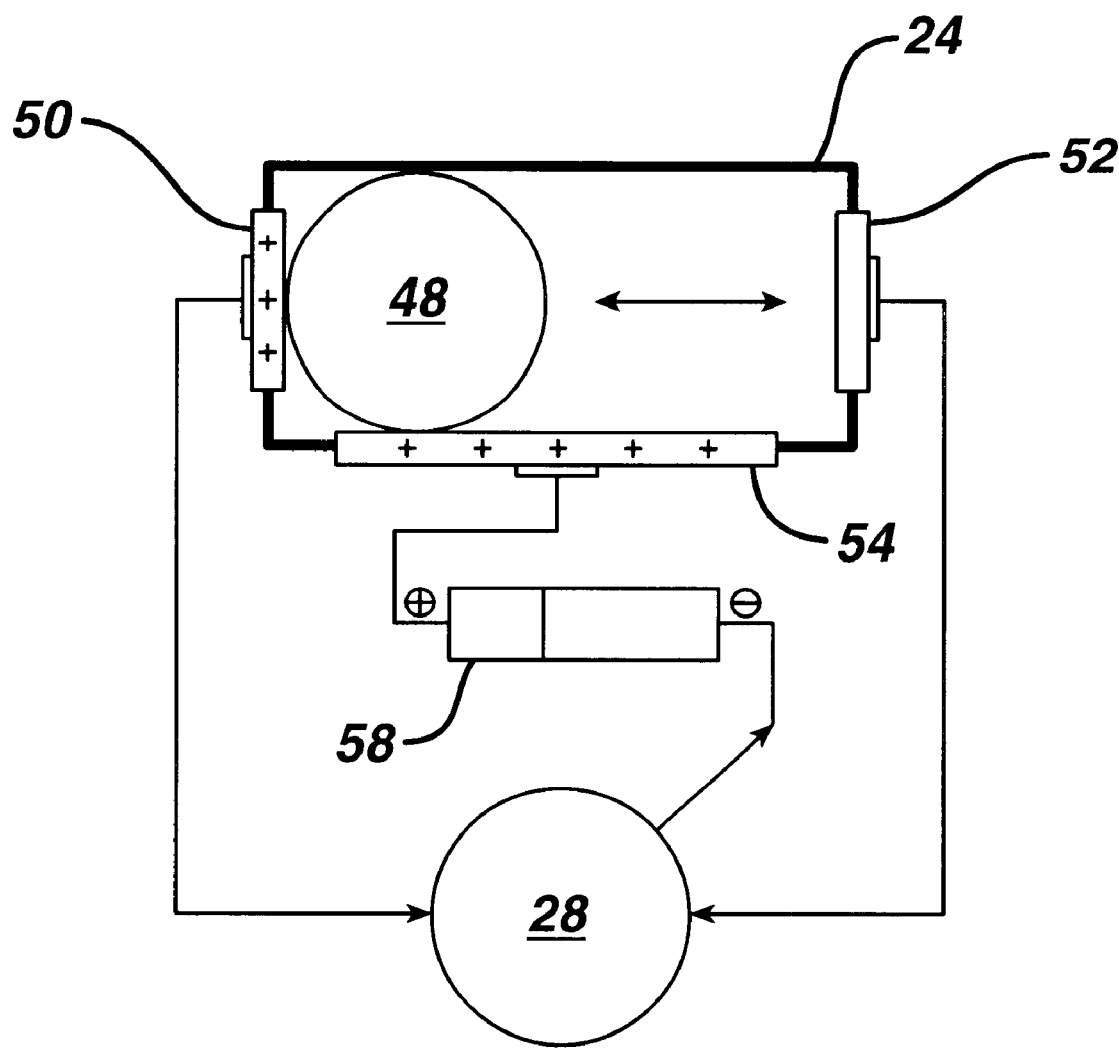
FIG. 5 discloses an alternative embodiment.

FIG. 5 discloses an alternative embodiment which gives more details of motion sensor 24, and eliminates microprocessor 26 and feedback sensor 27. Bi-directional motion sensor 24 includes a steel ball 48 and switch plates 50, 52 and 54. Ball 48 is always in contact with plate 54 and rolls between positions in contact with plates 50 or 52. When ball 48 is in contact with plate 50, drive mechanism 28 is turned on to rotate the tufts of bristles to a first position as described above. When ball 48 is in contact with plate 52, the drive mechanism is turned off, allowing a spring to rotate the tufts of bristles to a second position as described above. A battery 58 supplies electrical power.

Turning to FIGS. 6 and 7, a further alternative embodiment of the invention will be described. FIG. 6 shows a toothbrush 60 which is being moved in the direction of an arrow 62. A toothbrush user grips brush 60 by a slide handle 64. Handle 64 is mounted onto brush body 66 such that the handle can move back-and-forth relative to body 66 in the direction of arrow 62 and an arrow 68 (see FIG. 7). A switch 70 is connected to handle 64, and a compression,spring 72 presses switch 70 and handle 64 in the direction of arrow 62 to a first position shown in FIG. 6. In this position, switch 70 has disconnected an electrical power supply 74 from a solenoid 76. Switch 70 and solenoid 76 are connected by sliding electrical contacts.

A compression spring 78 is mounted on a drive shaft 80 between an internal wall 82 of body 66 and a forward end of solenoid 76. The drive shaft is connected to the solenoid. When the solenoid is deenergized as in FIG. 6, spring 78 presses the solenoid to the right, thus pulling the drive shaft to the right. This in turn rotates bristles 16 counter-clockwise to their position in FIG. 6 as described above.

Referring to FIG. 7, when the user moves handle 64 in the direction of arrow 68, brush 60 is also moved in this direction. This movement overcomes the force of spring 72 allowing handle 64 to move relative to body 66. In the position shown in FIG. 7, switch 70 has connected power supply 74 to solenoid 76. The energized solenoid moves to the left, overcoming the force of spring 78, and moves drive shaft 80 to the left. Such movement of the drive shaft causes bristles 16 to be rotated clockwise to their position shown in FIG. 7.

The invention has been described with reference to a preferred embodiment. However, it will be appreciated that variations and modifications can be effected by a person of ordinary skill in the art without departing from the scope of the invention.

We claim:

1. An oral care device, comprising:

a handle;

a head extending from the handle;

one or more oral care elements extending from the head; and a drive for engaging a base portion of each of the one or more oral care elements and for positioning each said oral care element relative to that portion of the head from which the oral care element projects based on the motion of the oral care device, wherein each oral care element is positioned to be angled towards a direction of motion of the oral care device.

2. The oral care device of claim 1, wherein each of the one or more oral care elements is a tuft of one or more bristles.

3. The oral care device of claim 1, wherein each of the one or more oral care elements is a nozzle for dispensing water, ultrasonic energy, an anti-bacterial laser or an anti-bacterial gas.

4. The oral care device of claim 1, wherein the drive includes a motion sensor for sensing motion of the oral care device and a microprocessor for receiving information from the motion sensor and using this information to control operation of the drive.

5. The oral care device of claim 1, wherein the positioning of each oral care element changes its angle relative to that portion of the head from which the oral care element projects.

6. The oral care device of claim 1, wherein each oral care element is positioned at or near the commencement of motion of the oral care device in said direction.

7. The oral care device of claim 1, wherein the direction of motion is substantially parallel to a long axis of the handle.

8. The oral care device of claim 1, wherein each oral care element is movable to a position which is angled by about 17 degrees to about 20 degrees from a line which extends in a perpendicular direction from that portion of the head from which each oral care element projects.

9. An oral care device, comprising:

a handle;

a head extending from the handle;

one or more oral care elements extending from the head; and means for engaging a base portion of each of the one or more oral care elements and for positioning each said oral care element relative to that portion of the head from which the oral care element projects based on the motion of the oral care device.

10. A method of adjusting an oral care device as it is being used, comprising the steps of:

providing an oral care device having a handle, a head extending from the handle, one or more oral care elements extending from the head, and a drive which engages a base portion of each of the one or more oral care elements;

automatically sensing the motion of the oral care device; and automatically adjusting the position of each said oral care element relative to that portion of the head from which the oral care element projects based on the motion of the oral care device to achieve enhanced oral care.

11. The method of claim 10, wherein the adjusting step changes the angle of each oral care element relative to that portion of the head from which the oral care element projects.

12. The method of claim 10, wherein the adjusting step positions each oral care element to be angled towards a direction of motion of the oral care device.

13. The method of claim 12, wherein the adjusting step positions each oral care element at or near the commencement of motion of the oral care device in said direction.

14. The method of claim 12, wherein the direction of motion is substantially perpendicular to a long axis of the handle.

15. The method of claim 10, wherein the adjusting step moves each oral care element to a position which is angled by about 17 degrees to about 20 degrees from a line which extends in a perpendicular direction from that portion of the head from which each oral care element projects.

* * * * *